US009326766B2

(12) United States Patent
Shields et al.

(10) Patent No.: US 9,326,766 B2
(45) Date of Patent: May 3, 2016

(54) NEEDLE DRIVER

(71) Applicants: John Martin Shields, Miami, FL (US); Syed Hussain, Cincinnati, OH (US)

(72) Inventors: John Martin Shields, Miami, FL (US); Syed Hussain, Cincinnati, OH (US)

(73) Assignee: Novasurg Innovations, LLC, Cincinnati, OH (US)

( * ) Notice: Subject to any disclaimer, the term of this patent is extended or adjusted under 35 U.S.C. 154(b) by 369 days.

(21) Appl. No.: 13/840,459

(22) Filed: Mar. 15, 2013

(65) Prior Publication Data

US 2014/0276978 A1    Sep. 18, 2014

(51) Int. Cl.
  *A61B 17/04*  (2006.01)
  *A61B 17/062*  (2006.01)

(52) U.S. Cl.
  CPC ........... *A61B 17/062* (2013.01); *A61B 17/0469* (2013.01); *A61B 17/04* (2013.01); *A61B 17/0482* (2013.01); *A61B 17/0625* (2013.01)

(58) Field of Classification Search
  CPC .................................................. A61B 17/062
  See application file for complete search history.

(56) References Cited

U.S. PATENT DOCUMENTS

| | | | |
|---|---|---|---|
| 532,306 A | 1/1895 | Brown | |
| 2,652,832 A | 9/1953 | Castroviejo | |
| 3,834,021 A | 9/1974 | White et al. | |
| 4,165,745 A * | 8/1979 | Heifetz | 606/174 |
| 4,345,601 A | 8/1982 | Fukuda | |
| 4,446,866 A | 5/1984 | Davison | |
| 4,491,135 A | 1/1985 | Klein | |
| 4,760,848 A | 8/1988 | Hasson | |
| 4,994,079 A * | 2/1991 | Genese et al. | 606/206 |
| 5,129,912 A | 7/1992 | Noda et al. | |
| 5,338,317 A | 8/1994 | Hasson et al. | |
| 5,405,353 A | 4/1995 | Randall | |
| 5,425,705 A * | 6/1995 | Evard et al. | 604/28 |
| 5,499,997 A | 3/1996 | Sharpe et al. | |
| 5,628,757 A * | 5/1997 | Hasson | 606/148 |
| 5,653,717 A | 8/1997 | Ko et al. | |
| 5,851,211 A | 12/1998 | Khoury | |
| 5,944,739 A | 8/1999 | Zlock et al. | |
| 5,951,575 A | 9/1999 | Bolduc et al. | |
| 5,954,733 A | 9/1999 | Yoon | |
| 6,077,278 A | 6/2000 | Mayer | |
| 6,102,920 A | 8/2000 | Sullivan et al. | |
| 6,149,642 A | 11/2000 | Gerhart et al. | |
| 7,137,988 B2 | 11/2006 | Frye | |
| 8,821,444 B2 | 9/2014 | Scheller et al. | |
| 2009/0157098 A1 * | 6/2009 | Meybodi | A61B 17/8861 606/139 |
| 2011/0106111 A1 | 5/2011 | Yang et al. | |

(Continued)

OTHER PUBLICATIONS

International Search Report and Written Opinion dated Oct. 10, 2014, for corresponding International Application Serial No. PCT/US2014/27955, filed Mar. 14, 2014 (13 pages).

*Primary Examiner* — Robert Lynch

(74) *Attorney, Agent, or Firm* — Bradley D. Beck; Daniel F. Nesbitt; Hasse & Nesbitt LLC

(57) ABSTRACT

A needle driver, comprising a first elongated body having a substantially hollow interior portion and a first and second end, a second elongated body having a substantially hollow interior portion slideably disposed in the first elongated body, a clamping device having a clamping end and a connected end, the clamping device at least partially disposed in the first elongated body and in the second elongated body, wherein the connected end is affixed to the first elongated body, and a slideable actuator affixed to the second elongated body.

7 Claims, 15 Drawing Sheets

(56) References Cited

U.S. PATENT DOCUMENTS

| | | | |
|---|---|---|---|
| 2012/0059394 A1* | 3/2012 | Brenner | A61B 1/00087 606/142 |
| 2012/0143223 A1 | 6/2012 | Woodard, Jr. et al. | |
| 2012/0289975 A1 | 11/2012 | Martin et al. | |
| 2013/0085326 A1 | 4/2013 | Scheller et al. | |
| 2014/0343528 A1 | 11/2014 | Scheller | |

* cited by examiner

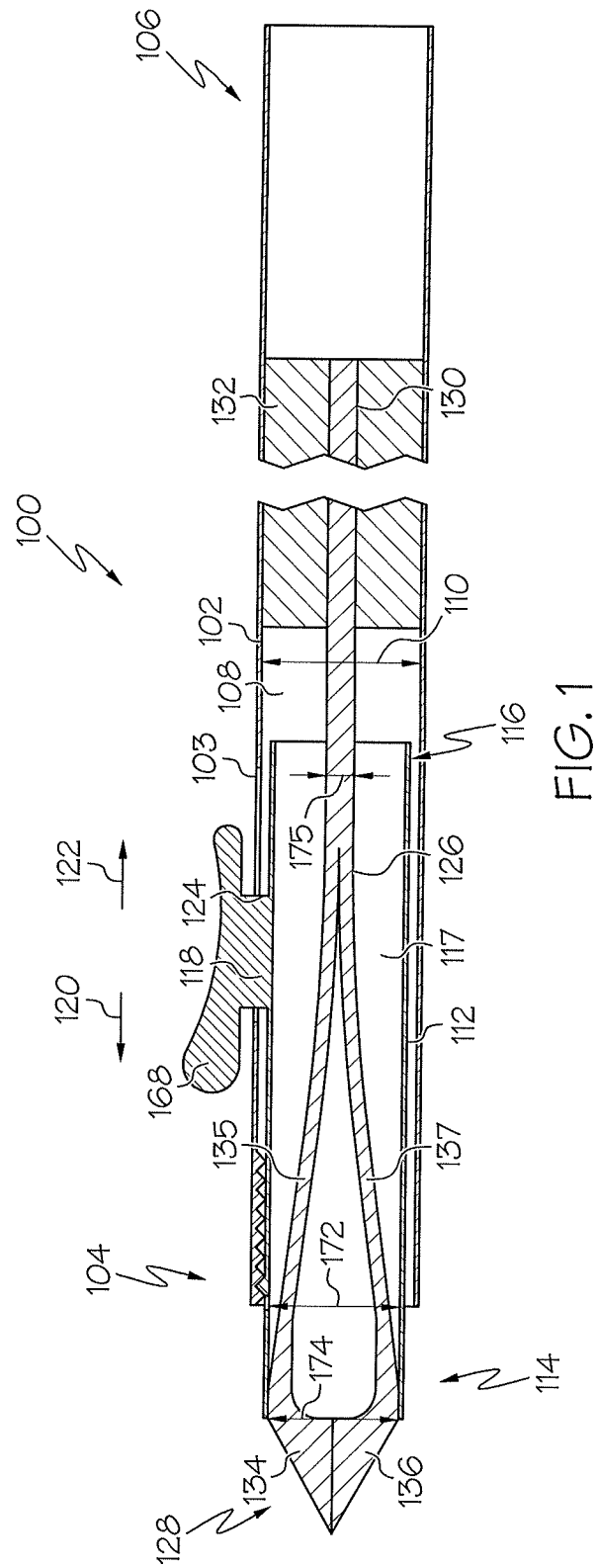

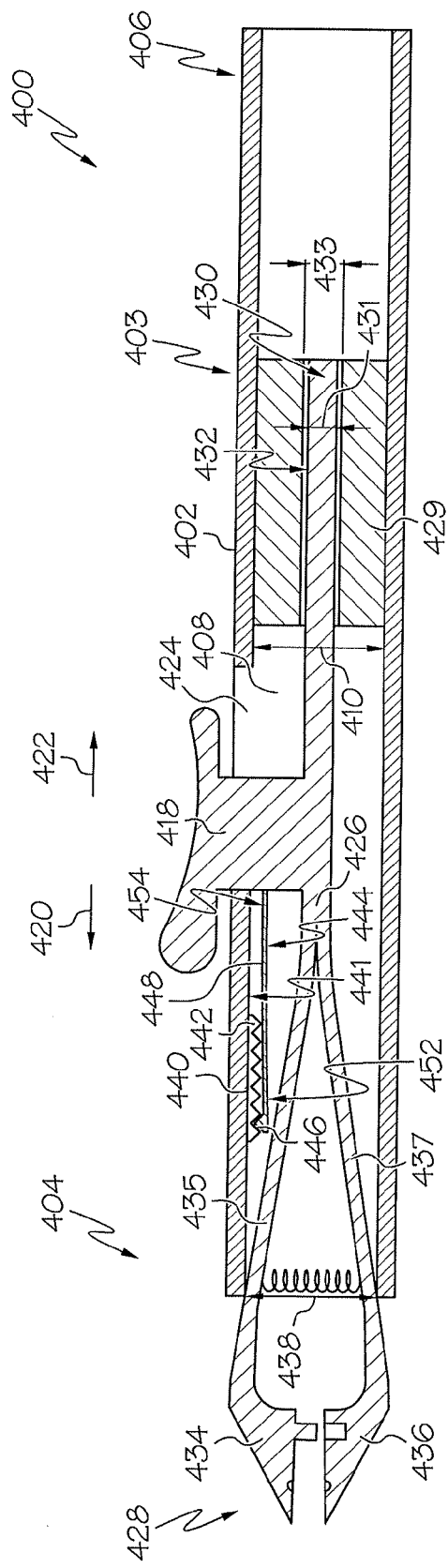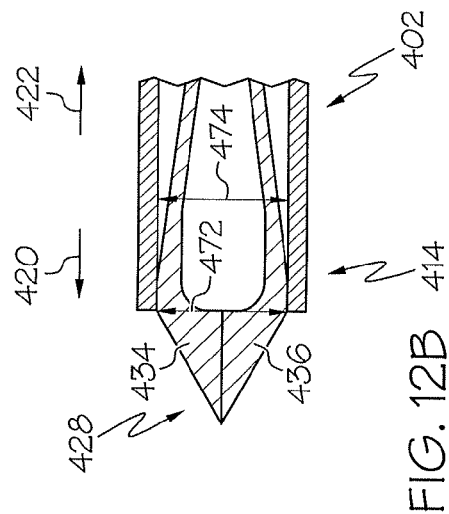
FIG. 12A
FIG. 12B

NEEDLE DRIVER

FIELD OF INVENTION

This invention relates to a needle driver with a clamping device. Specifically, this invention relates to a needle driver having a slideable actuator to operate the clamping device.

BACKGROUND OF THE INVENTION

Suturing is commonly known as the practice of using lengths of medical suture material to ligate or approximate tissue for proper healing after a surgical or other type of invasive medical procedure involving an incision. The process of suturing bodily tissue upon completion of a medical procedure, whether the particular procedure is open, endoscopic, laparoscopic, or another type of procedure, generally encompasses a substantial portion of the respective procedure time. In open-type surgical procedures, which refers to a procedure wherein the surgeon gains access to a surgical site via a relatively large incision, for example, the sutures required to properly ligate such an incision can easily take tens of minutes to properly and carefully apply. In endoscopic and/or laparoscopic type procedures, which generally refers to minimally invasive-type surgical procedures wherein the surgeon gains access to the surgical site via one or more small tissue portals/incisions, the suturing processes may be substantially more complicated, as the surgeon generally has a diminished view of an internal suturing site as well as a substantially reduced physical space for manipulating the respective suturing equipment. Therefore, the time required to suture in these internal-type situations is generally substantially longer than in open-type procedures, in addition to being substantially more difficult for the surgeon to accomplish.

In conventional medical techniques, suturing processes have generally been accomplished with the use of a sharp suture needle carrying a length of suture material, wherein the suture needle is caused to penetrate and pass through the tissue while simultaneously pulling the suture material therethrough. Once the suture material has been pulled through the tissue, the surgeon ties a knot in the suture material and secures the suture. Conventional needle drivers require the surgeon to grip the needle with the jaw portion of the needle driver, possibly locking jaws in tension with a ratchet mechanism in the handle portion, and thereafter, manipulate the needle so as to create sutures. The surgeon may engage and control the needle driver via placement of the appropriate fingers within the respective handle finger holes.

However, a surgeon's manipulation of the conventional needle driver is limited by the physical configuration of the conventional needle driver. For example, as a result of the surgeon having at least one finger placed in the finger holes, the surgeon's ability to manipulate/rotate the needle driver about a longitudinal axis of the needle driver is limited. As such, movements often require the surgeon to go through odd and/or uncomfortable motions, such as elevation of the surgeon's elbow corresponding to the hand having the needle driver therein upward in order to engage tissue with the needle. This process is known to cause strain and fatigue on a surgeon during suturing, and therefore, presents a potential for fatigue and/or strain based error. Additionally, the configuration of the jaws of conventional needle drivers results in the optimal gripping force being obtained when the jaws of the needle driver are completely closed. Inasmuch as a needle may not be gripped by the needle driver when the jaws are closed, as there is no physical space between the jaws in this position, conventional devices are not capable of gripping the needle with the optimal force available from the respective driver.

The shortcomings of conventional needle drivers are exacerbated when used in connection with microsurgery and endoscopic surgery, as these types of procedures require additional time and surgical effort to complete as a result of the nature of the surgical procedures. This can unduly prolong the duration of surgery, and therefore, prolong the period in which the patient is under anesthesia, which is undesired. Further, as a result of the less than optimal needle gripping force available from conventional devices, surgeons often have difficulty in maintaining a suture needle within the jaws of conventional devices, which may result in dropping a needle. Nevertheless, endoscopic surgery is often preferred over open surgery due to the ability to reduce incision trauma and facilitate wound healing, which directly results in cost savings associated with shorter hospital stays and performing surgery in non-hospital and/or out-patient surgery sites.

There exists a need for a needle driver that provides improved ergonomic characteristics over conventional devices so that the needle driver may be easily manipulated by the surgeon with minimal stress and/or fatigue.

SUMMARY OF THE INVENTION

The invention relates to a needle driver, comprising a first elongated body having a substantially hollow interior portion and a first and second end, a second elongated body having a substantially hollow interior portion slideably disposed in the first elongated body, a clamping device having a clamping end and a connected end, the clamping device at least partially disposed in the first elongated body and in the second elongated body, wherein the connected end is affixed to the first elongated body, and a slideable actuator affixed to the second elongated body.

The invention also relates to a needle driver, comprising a first elongated body having a substantially hollow interior portion, and a first and second end, a second elongated body slideably disposed in the first elongated body and having a substantially hollow interior portion, a clamping device having a clamping end and a connected end, the clamping device at least partially disposed in the first elongated body and in the second elongated body, wherein the connected end is affixed to the first elongated body, and a rotatable actuator rotatably affixed to the first elongated body and engaging with the second elongated body.

The invention further relates to a needle driver comprising an elongated body having a substantially hollow interior portion and a first and second end, a clamping device having a clamping end and a connected end, the clamping device slideably and at least partially disposed in the elongated body, and a slideable actuator affixed to the clamping device.

DETAILED DESCRIPTION OF THE DRAWINGS

FIG. 1 is a section view of a needle driver of the invention with the jaws in the closed position.

FIG. 9B is a perspective view of the needle driver of FIG. 9a.

FIG. 12A is a section view of another embodiment of a needle driver of the invention.

FIG. 12B is a partial sectional view of a first end of the needle driver of FIG. 12A with the jaws in the clamping position.

DETAILED DESCRIPTION OF THE INVENTION

Figure 2A:
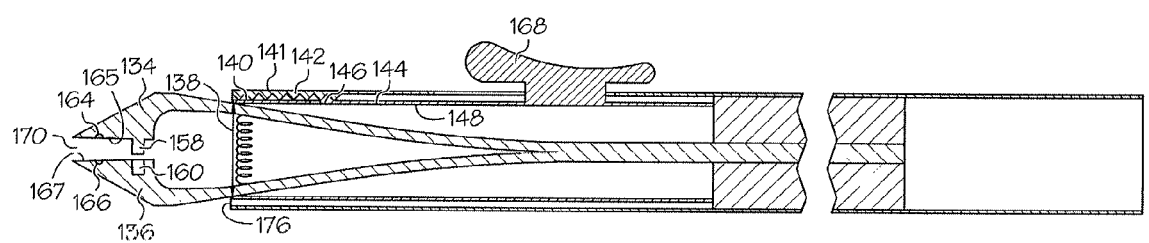
FIG. 2A is a section view of the needle driver of FIG. 1 with the jaws in the open position.
Figure 3:
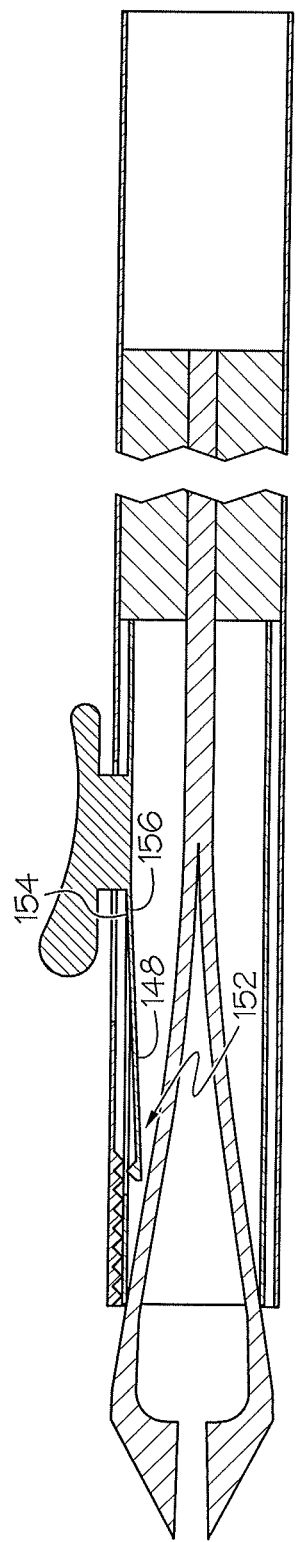
FIG. 3 is a section view of the needle driver of FIG. 1 with the lock in an unlocked position.

FIG. 1 shows one embodiment of a needle driver 100 of the invention. The needle driver 100 has a first elongated body 102 having a first, distal end 104 and a second, proximal end 106. At least a portion of the first elongated body 102 has a substantially hollow interior portion 108 defined by an interior dimension 110. An outer surface 103 of the first elongated body 102 may be knurled to allow the user to maintain a positive grip on the needle driver. Slideably disposed in the first elongated body 102 is a second elongated body 112 having a first, distal end 114, a second, proximal end 116, and a substantially hollow interior portion 117. The second elongated body 112 is slideable between a rearward, retracted position and a forward, extended position. The first, distal end 114 of the second elongated body 112 extends beyond the first, distal end 104 of the first elongated body 102 when the second elongated body 112 is in the forward, extended position, as shown in FIG. 1. The first, distal end 114 of the second elongated body 112 is disposed within the first distal end 104 of the first elongated body 102 when the second elongated body 112 is in the rearward retracted position, as shown in FIGS. 2A and 3. An actuator 118 is affixed to the second elongated body 112 for moving the second elongated body 112 forward and backward in the direction of arrows 120 and 122, respectively. The actuator 118 passes through a slot 124 in the first elongated body 102, which allows the actuator 118 to slide forward and backward in the directions of arrows 120 and 122, respectively. A digit receiver 168 designed for receiving a thumb, index finger, or other digit of the user may be affixed to the actuator 118.

At least partially disposed in the second elongated body is a clamping device 126 having a clamping end 128 and a connecting end 130. The connecting end 130 of the clamping device 126 is affixed to the inside of the first elongated body 102 with a connector 132. The clamping end 128 of the clamping device has a first jaw member 134 and a second jaw member 136 opposing the first jaw member 134. First arm 135 and second arm 137 connect the connected end to the first jaw member and second jaw member. The arms taper from a larger external dimension 174 to a smaller external dimension 175 between the clamping end and the connecting end.

Typically, the first jaw member and the second jaw member are biased away from each other when they are in the relaxed position, as shown in FIG. 2A. Various methods can be used to bias the first and second jaw members away from each other. For example, the material used to make the clamping device may be a spring steel that will allow the first and second jaws to flex inward and outward. Alternatively, a spring 138 may be disposed between the first arm 135 and the second arm 137.

As shown in FIG. 1, an internal dimension 172 of the first end 114 of the second elongated body is approximately the same as an external dimension 174 of the first and second jaw members when the jaw members are in a closed position. As such, when the second elongated body is in a most forward position after being pushed in the direction of arrow 120, it biases the first jaw member and the second jaw member towards each other, causing the jaw members to move towards each other and clamp. When the actuator is moved in the direction of arrow 122, the second elongated body slides in the direction of arrow 122 and away from the clamping end 128. Because of the taper in the arms between the clamping end and the connecting end, the first and second jaw members bias away from each other as the second elongated body 112 is retracted in the direction of arrow 122.

Figure 2B:
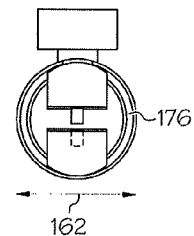
FIG. 2B is an end view of the needle driver of FIG. 1 with the jaws in the open position.

A serrated edge 140 having teeth 142 is disposed on an interior portion 141 of the first, distal end 104 of the first elongated body 102. Affixed to the actuator 118 is a locking device 144 with a tooth 146 that mates with the teeth 142 disposed in the first, distal end 104 of the first elongated body 102. Here, the locking device 144 is a flexible bar 148 with a tooth 146 on a distal end 152 of the flexible bar 148. As shown in FIG. 3, a proximal end 154 of the flexible bar 148 is affixed to an interior portion 156 of the second elongated body 112 and connects the tooth 146 with the second elongated body 112. The first elongated body 102 and the second elongated body 112 can cooperate to define an annular space 176, as shown in FIGS. 2A and 2B. The teeth 142 of the serrated edge 140 can extend inwardly from the interior portion 141 first, distal end 104 of the first elongated body 102 into the annular space 176. Alternatively, there may be a single tooth disposed on the interior portion 141 of the first elongated body and multiple teeth disposed on the distal end 152 of the flexible bar 148.

Figure 4:
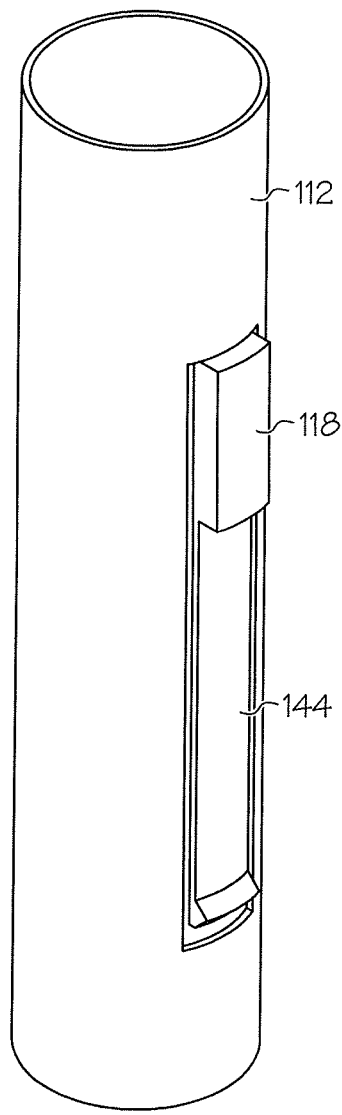
FIG. 4 is a top view of one embodiment of a second elongated body of the invention.
Figure 5:
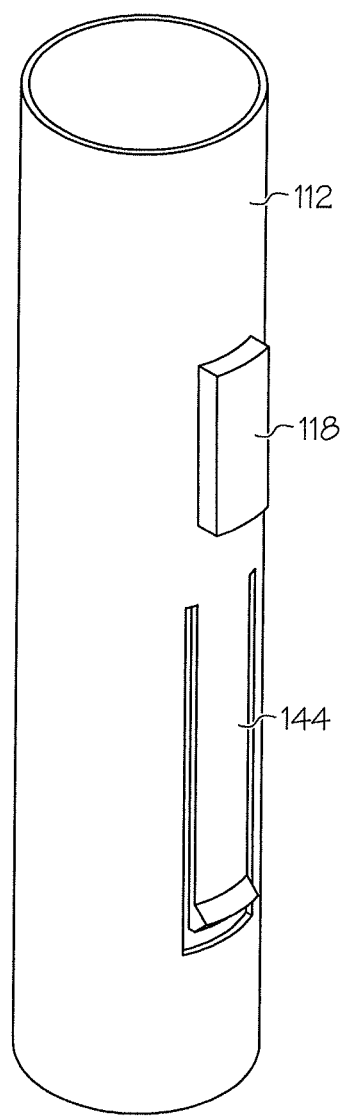
FIG. 5 is a top view of another embodiment of a second elongated body of the invention.

Alternatively, the locking device 144 may be stamped or otherwise formed from the second elongated body 112, as shown in FIG. 4. In this example, the second elongated body is made from a material, such as spring steel, that is resilient and flexible. The actuator 118 is mounted to the flexible bar 148 of the locking device. By pressing down on the actuator, the operator disengages the tooth 146 of the flexible bar 144 from the teeth 142 located on the interior portion of the first elongated body 102. Alternatively, the flexible bar may not be cut back as far as the actuator, as shown in FIG. 5. In the embodiment of FIG. 5, the flexible bar does not extend back to the actuator. In this situation, the tension of the flexible bar and the engagement of its tooth with the teeth of the interior portion of the first elongated body are overcome when the operator slides the actuator in the direction of arrow 122 in FIG. 1. The actuator 118 shown in FIGS. 4 and 5 may also have a digit receiver as shown in FIG. 2A.

As shown in FIG. 2A, the first jaw member 134 may have a pin 158 that aligns with a hole 160 having a diameter sized to receive the pin 158 and located in the second jaw member 136. The pin and hole align the jaws in the lateral direction, represented by arrow 162 in FIG. 2B, so that the jaws do not slide apart in the lateral direction when grasping an item. Alternatively, the second jaw member 136 may have the pin and the first jaw member 134 may have the hole for receiving the pin.

The jaws may also have a relief for receiving a tool such as a needle. As shown in FIG. 2A, the first jaw 134 has a relief 164 on gripping portion 165 and the second jaw 136 has a relief 166 on a gripping portion 167. Typically, the reliefs are sized to fit the intended tool, such as a needle and are cut in a shape to match the tool. For example, if the jaws were made to hold a round needle, the relief 164 would be a semicircle and the relief 166 would be a semicircle. Alternatively, only one jaw may have a relief for grasping a tool and the other jaw may not have a relief. In addition, the gripping portions 165 and 167 of the jaws may be knurled or grated to improve gripping performance. The knurling or grating may be in addition to the reliefs. While the jaws described here are typically used for holding needles, other types of jaws may also be used when required to grasp other tools, instruments, materials or tissue. For example, blunt jaws may be used when the operator desires to grab or manipulate tissue and minimize tissue damage.

In operation, a user holds the first elongated body in a hand with a digit on the digit receiver 168. To open the closed jaws shown in FIG. 1, the user slides the digit receiver in the direction of arrow 122, thereby sliding the second elongated body 112 in the direction of arrow 122. The tension in the arms 135 and 137, or the spring 138, which bias the first jaw member and second jaw member away from each other, causes the first and second jaw members to separate thereby creating a gap 170 between them. The user then inserts a tool, such as a needle for suturing, between the first jaw member and the second jaw member and moves the actuator 118 with the digit receiver 168 in the direction of arrow 120 to clamp the tool between the first and second jaws.

As the actuator 118 is moved in the direction of arrow 120, the tooth 146 on the flexible arm 148 engages with the teeth 142 on the serrated edge 140 located on the interior portion 141 of the first end 104 of the first elongated body 102. The actuator can be locked in a predetermined number of positions depending on where the tooth 146 aligns with the teeth of the serrated edge. In this manner, the user can adjust the clamping force on the tool and can grasp, secure, and lock tools of a varying size between the first and second jaws.

After locking the needle between the jaws, the user can easily manipulate the needle driver by rolling it between his fingers, with the knurled surface of the first elongated body providing a positive grip surface and reducing slippage between the needle driver and the user's fingers. While the first elongated body is typically cylindrical, it could also be multi-sided, such as square, hexagonal, or octagonal. Various shapes could be provided, depending on the users' preferences.

Figure 11:
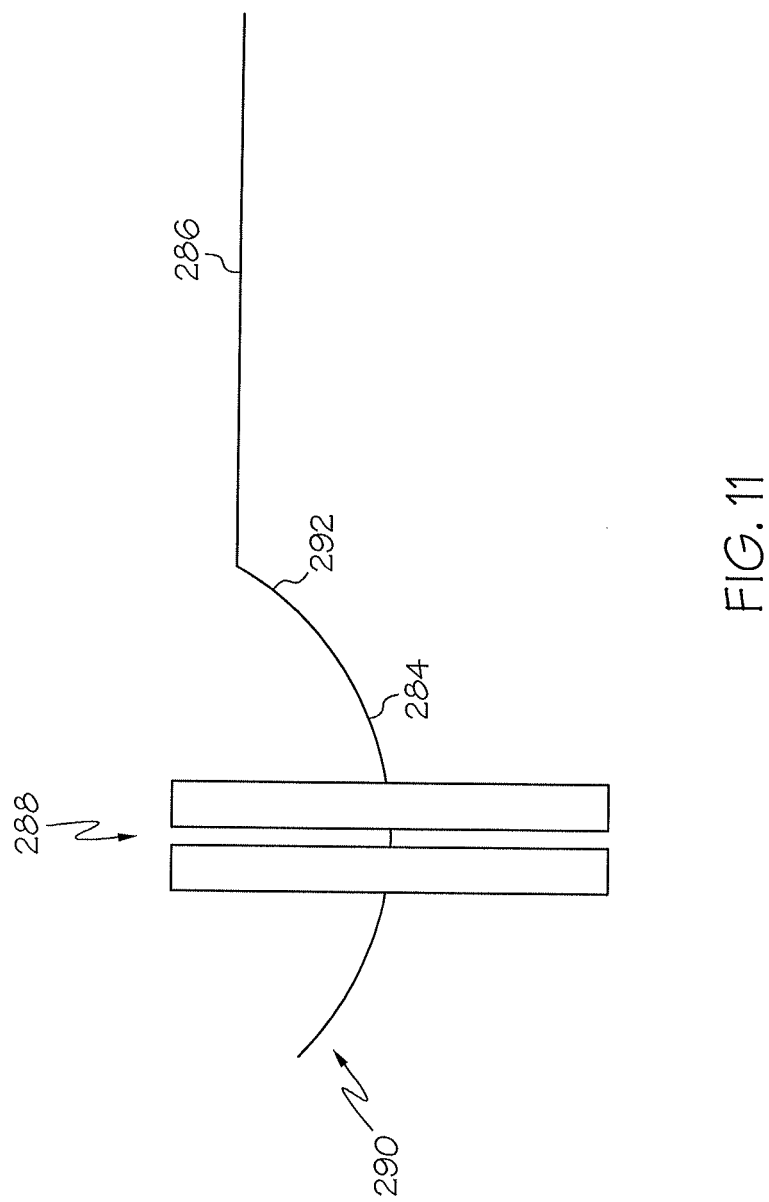
FIG. 11 is a side section view of a needle suturing tissue.

FIG. 11 shows a needle 284 with suture thread 286 being used to suture tissue 288. The needle 284 has a forward end 290 and a rearward end 292. Once the rearward end 292 of the needle is locked in the jaws, the user typically proceeds with suturing by driving the needle through the tissue with the needle driver. Once the needle passes through and the forward end of the needle is exposed on the far side of the tissue, the user releases the needle from the needle driver by pushing down on the actuator to disengage the tooth 146 from the serrated edge 140 and sliding the actuator back in the direction of arrow 122, or by sliding the actuator in the direction of arrow 122 and allowing the tooth 146 to ratchet over the serrated edge 140. The user then grabs the forward end 290 of the needle with the needle driver, locks the jaws on the forward end of the needle, and pulls the needle through the tissue. To ready the needle for the next suture, the needle is released from the needle driver and is then grasped by the needle driver at the rearward end of the needle. The needle is then driven through the tissue and the process is repeated.

Figure 6:
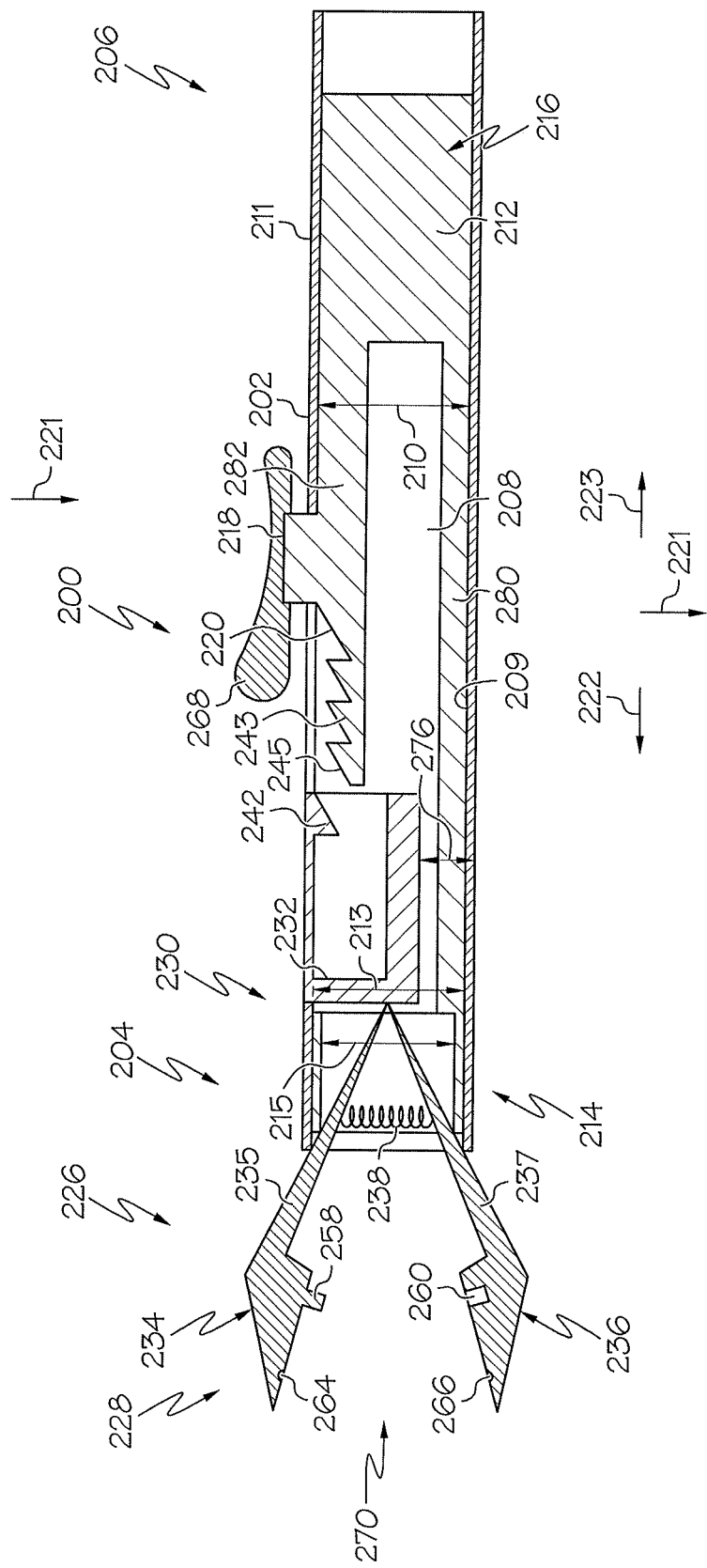
FIG. 6 is a section view of another needle driver of the invention with the jaws in the open position.

FIG. 6 shows another embodiment of a needle driver 200. The needle driver 200 has a first elongated body 202 having a first end 204 and a second end 206. At least a portion of the first elongated body 202 has a substantially hollow interior portion 208 defined by an interior dimension 210. As before, an outer surface 211 of the first elongated body 202 may be knurled to allow the user to maintain a positive grip on the needle driver.

At least partially disposed in the substantially hollow portion of the first elongated body 202 is a second elongated body 212 having a first end 214, a second end 216, and an actuating mechanism 218 and a locking device 220 disposed therebetween. The first end 214 of the second elongated body 212 includes a substantially hollow interior portion with an external dimension 213 slightly less than the internal dimension 210 of the first elongated member and an internal dimension 215 sized to slide over and operate a clamping device 226. A bar 280 connects the first end 214 of the second elongated body 212 to the second end 216 of the second elongated body. The second end of the second elongated body 212 has a flexible elongated bar 282 connected to it.

The flexible elongated bar 282 includes the actuating mechanism 218 and locking device 220. The locking mechanism has an engaging section 243 for mating with a receiver 242 located in the connector 232 (described later). The actuating mechanism 218 is used to move the flexible elongated bar 282 to engage and disengage the locking device 220 from the receiver 242.

Disposed in the second elongated body is the clamping device 226 having a clamping end 228 and a connecting end 230. The clamping end 228 of the clamping device has a first jaw member 234 and a second jaw member 236 opposing the first jaw member. First arm 235 and second arm 237 join the connecting end 230 to the first jaw member and second jaw member. The connecting end 230 of the clamping device 226 is affixed to the inside of the first elongated body 202 with the connector 232 which is disposed in the first end 204 of the elongated body 202.

Figure 8B:
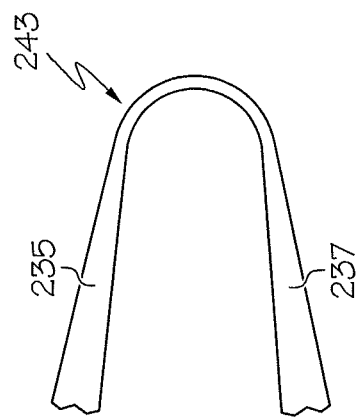
FIG. 8B is a section view of another connecting end of a clamping device of the invention.
Figure 8A:
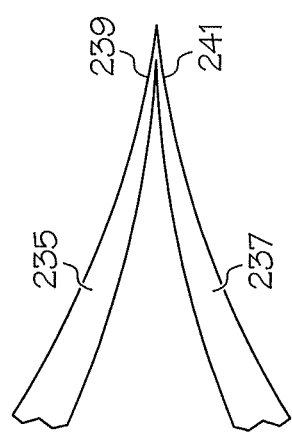
FIG. 8A is a section view of a connecting end of a clamping device of the invention.

Typically, the first jaw member 234 and the second jaw member 236 are biased away from each other when they are in the relaxed position, as shown in FIG. 6. Various methods can be used to bias the first and second jaw member away from each other. For example, the material used to make the clamping device may be a spring steel that will allow the first and second jaw members to flex inward and outward. End 239 of the first arm 235 and end 241 of the second arm 237 may be fused together as shown in FIG. 8A to cause the first jaw member 234 and the second jaw member 236 to bias away from each other. Also, clamping device 226 may be made from a single piece of material with the connecting end 230 bent to create a spring 243 as shown in FIG. 8B. Alternatively, a spring 238 may be disposed between the first arm 235 and the second arm 237 as shown in FIG. 6.

The connector 232 is sized to fit inside the substantially hollow portion 208 of the first elongated body 202 and is spaced a distance 276 from an interior surface 209 of the first elongated body to allow the bar 280 to pass between the connector 232 and the interior surface 209. The connector 232 defines a hollow interior portion 231 sized to receive the engaging section 243 of the flexible elongated bar 282. Disposed in the hollow interior portion 231 is a receiver 242 that mates with the engaging section 243 of the locking device 220. In this embodiment, the receiver 242 is a tooth and the engaging section 243 is a serrated edge that mates with the tooth. Other locking mechanisms may also be used. For example, the receiver could be a serrated edge that mates with a tooth of the engaging section.

Similar to the embodiment described previously, the first jaw member 234 may have a pin 258 that aligns with a hole 260 with a diameter sized to receive the pin located in the second jaw member 236 to align the jaws in the lateral direction. Alternatively, the second jaw member 236 may have the pin and the first jaw member 234 may have the hole for receiving the pin.

The jaws may also have a relief for receiving a tool such as a needle. As shown in FIG. 6, the first jaw 234 has a relief 264 and the second jaw 236 has a relief 266. Typically, the reliefs are sized to fit the intended tool, such as a needle and are cut in a shape to match the tool. For example, if the jaws were made to hold a round needle, the relief 264 would be a semicircle and the relief 266 would be a semicircle. Alternatively, only one jaw may have a relief for grasping a tool and the other jaw may not have a relief.

Figure 7A:
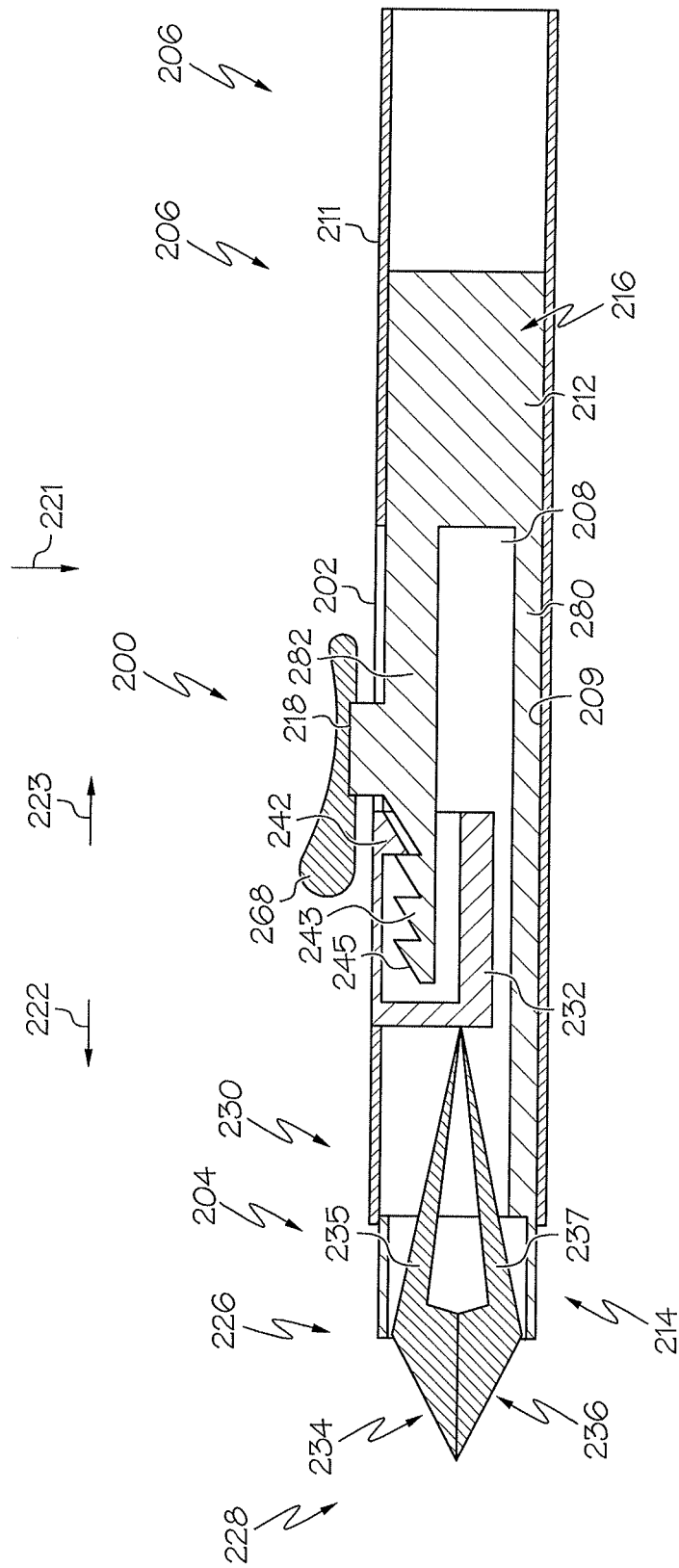
FIG. 7A is another section view of the needle driver of FIG. 6 with the jaws in the closed position.
Figure 7B:
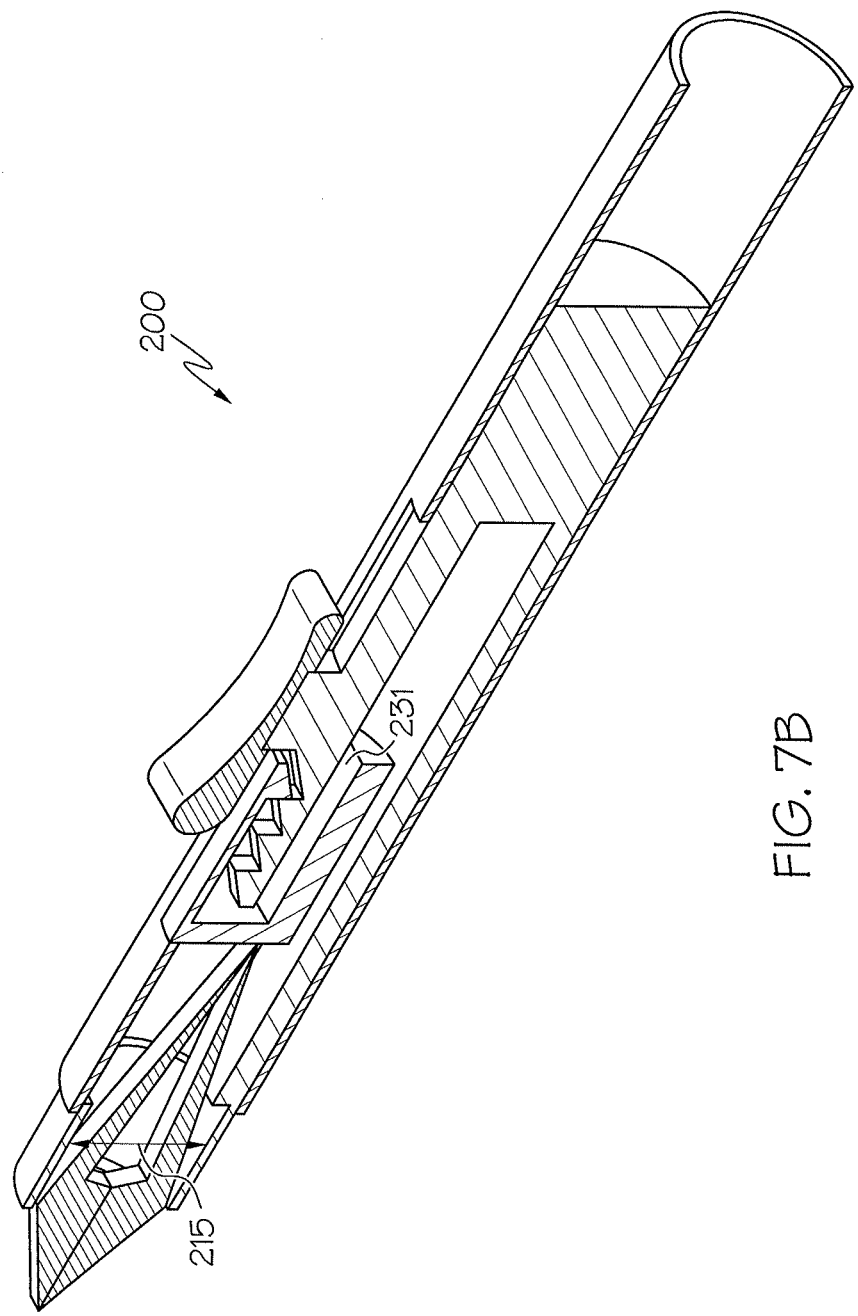
FIG. 7B is a perspective view of the needle driver of FIG. 6.

In operation, a user holds the first elongated body in a hand with a digit on a digit receiver 268. If the opposing jaws are closed, as shown in FIG. 7A, the user pushes the digit receiver in the direction of arrow 221 to disengage the engaging section 243 from the receiver 242 and then slides the digit receiver in the direction of arrow 223, thereby sliding the second elongated body 212 in the direction of arrow 223. The tension in the arms, or the spring 238, which bias the first jaw member and second jaw member away from each other, cause the first and second jaw members to separate creating a gap 270 between them. The user then inserts a tool, such as a needle for suturing, between the first jaw member and the second jaw member and moves the actuator 218 in the direction of arrow 222 to clamp the tool between the first and second jaws.

As the actuator 218 is moved in the direction of arrow 222, a tooth 245 of the engaging section 243 on the flexible elongated bar 282 engages with the receiver 242 located on the interior portion 231 of the connector 232. The actuator can be locked in a predetermined number of positions depending on where the receiver 242 aligns with the teeth of the engaging section 243 of the flexible elongated bar 282. In this manner, the user can adjust the clamping force on the tool and can grasp, secure, and lock tools of a varying size between the first and second jaws. Grasping and releasing a tool and suturing are completed as described in the earlier embodiment.

Figure 9A:
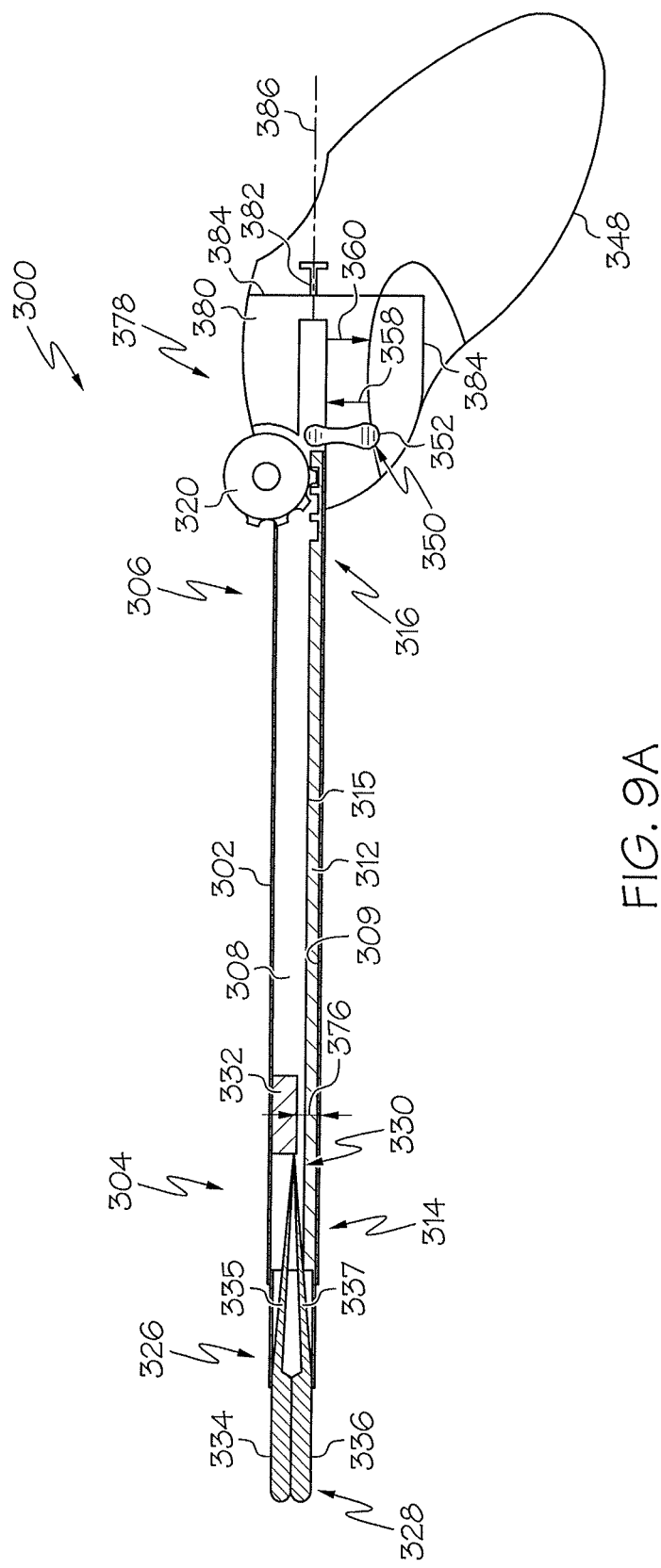
FIG. 9A is a section view of another embodiment of a needle driver of the invention.
Figure 9B:
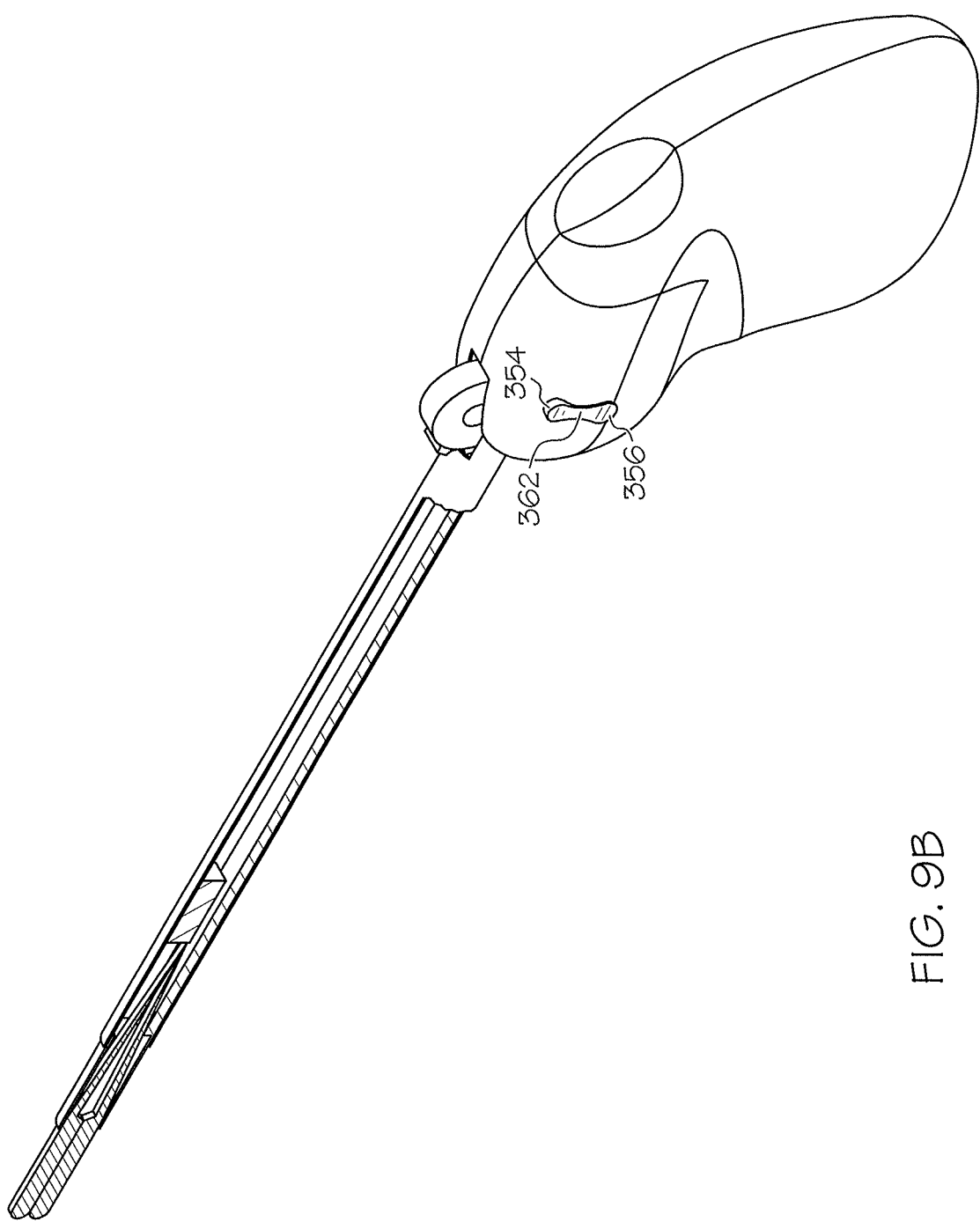

Another embodiment is shown in FIGS. 9A and 9B. The needle driver 300 could be used in traditional surgery or in laparoscopic surgery. The needle driver 300 has a first elongated body 302 having a first end 304, a second end 306, and a substantially hollow interior portion 308. At least a portion of the first elongated body has a substantially hollow portion 308. Slideably disposed in first elongated body 302 is a second elongated body 312 having a substantially hollow first end 314 and a second end 316. A connector 332 is sized to fit inside the substantially hollow portion 308 of the first elongated body 302 and is spaced a distance 376 from an interior surface 309 of the first elongated body to allow shaft 315 to pass between the connector 332 and the interior surface 309.

Figure 10:
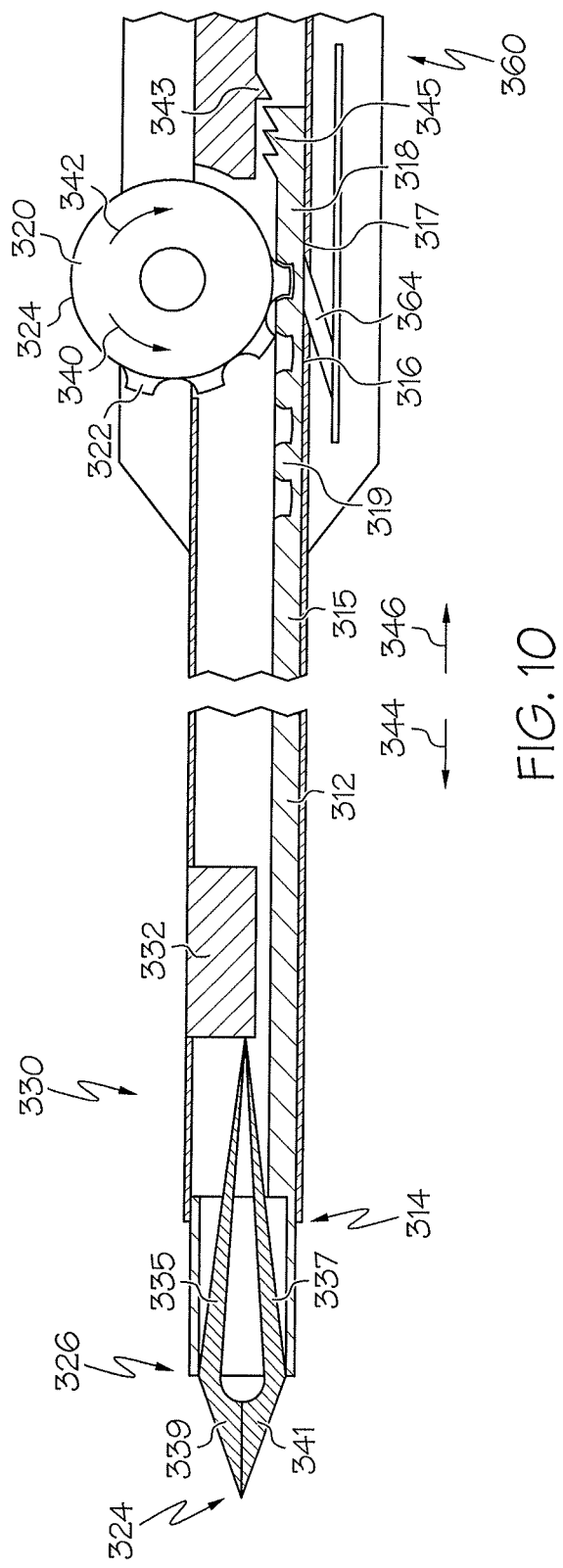
FIG. 10 is a section view of another embodiment of the needle driver of the invention.

As shown in FIGS. 9A, 9B, and 10, disposed in the first elongated body 302 is a clamping device 326 having a clamping end 328 and a connecting end 330. The connecting end 330 of the clamping device 326 is affixed to the inside of the first elongated body 302 with a connector 332. The clamping end 328 of the clamping device has a first jaw member 334 and a second jaw member 336 opposing the first jaw member. First arm 335 and second arm 337 connect the connected end 314 to the first jaw member and second jaw member. The jaws may be made to spring apart by any of the methods described previously, may have the pin and hole alignment mechanism described previously, and may have the reliefs for holding a tool as described previously. The jaws 334 and 336 shown in FIG. 9A are blunted to avoid tissue damage. The jaws 334 and 336 are typically used for holding and moving tissue instead of operating tools, such as needles. Alternatively, the jaws could be first jaw 339 and second jaw 341 designed to hold tools similar to the jaws 134 and 136 of FIG. 2A. Additionally, the blunt jaws 334 and 336 could be used instead of the tool holders on the other embodiments shown herein.

A handle 348 may be disposed on the second end 306 of the first elongated body 302. The handle allows the user to grasp and maneuver the needle driver by palming the driver. Disposed on the side of the handle is a lock 350 that is used to lock the shaft 315 in a certain position, thereby locking the jaws in a certain position. For example, the lock may be used to lock the jaws in an open position, in a closed or clamping position, or in an intermediate position. The lock may be a slide, a pivoting push button lock, or other type of lock. As a slide lock, the user slides a lock button 352 upward in the direction of arrow 358, which causes the lock to engage with the shaft 315 and prevent the shaft from moving until the lock button is slid downward in the direction of arrow 360, thereby unlocking the shaft. In an alternative design, the button may be slid downward in the direction of arrow 360 to lock the shaft and upward in the direction of arrow 358 to unlock the shaft. In a design shown in FIG. 9B, the lock button 352 pivots about its center 362. To lock the shaft 315, the user pushes the upper portion 354 of the lock button 350 inward towards the handle 348, causing the upper portion of the lock button to move inwardly towards the handle and a lower portion 356 of the lock button to move outwardly away from the handle. To unlock the shaft 315, the user pushes the lower portion 356 of the lock button 352 inwardly toward the handle.

The first end 314 of the second elongated body 312 is constructed similar to those described previously to slide over the first and second jaw members to open and close the first and second jaw members. The first end 314 and the second end 316 are connected by a shaft 315. The second end 316 of the driver includes a rack 318 with a first set of teeth 319 that mates with a second set of teeth 322 disposed on a perimeter 324 of a rotatable actuator 320. A spring 364 biases against an underside 317 of the rack 318 to hold the rack against the rotatable actuator 320. When the operator pushes the rotatable actuator 320 down, it compresses spring 364 and unlocks a tooth 343 from teeth 345. When the actuator is rotated in the direction of arrow 340, typically with one of the user's digits such as a finger or thumb, the shaft 315 moves in the direction of arrow 346, thereby sliding the second end 316 of the driver in the direction of arrow 346 and allowing the jaws 334 and 336 to open. When the actuator is rotated in the direction of arrow 342, the shaft 315 moves in the direction of arrow 344, thereby sliding the second end of the driver in the direction of arrow 344 and closing the jaws 334 and 336. While not shown in FIG. 10, a handle such as handle 348 of FIG. 9A, is typically included in the second end 360. Alternatively, a handle with a bulbous end such as that shown in FIG. 13 may be disposed on the second end 360.

Referring back to FIG. 9A, another embodiment has an operating portion 378 comprising the lock 350, the actuator 320, the first elongated body 302, the clamping device 326, and a body 380 may be connected to the handle 348 and rotate on a pin 382. A parting line 384 shows the separation between the operating portion 378 and the handle 348. The operating portion 378 pivots about a center axis 386 of the pin 382. In this embodiment, a user can hold the handle 348 in a palm and rotate the operating portion 378 with digits to thereby rotate the clamping device 326 relative to the first elongated body without having to rotate the entire needle driver 300.

FIG. 12A shows another embodiment of a needle driver 400 of the invention. The needle driver has an elongated body 402 having a first end 404 and a second end 406. At least a portion of the first elongated body has a substantially hollow portion 408 defined by an interior dimension 410. An outer surface 403 of the first elongated body may be knurled to allow the user to maintain a positive grip on the needle driver. Slideably disposed in the elongated body 402 is an actuator 418 affixed to a clamping device 426. The actuator passes through a slot 424 in the elongated body 402, which allows the actuator to slide forward and backward in the direction of arrows 420 and 422 respectively.

The clamping device 426 has a clamping end 428 and a guiding end 430. The guiding end 430 of the clamping device 426 slides in a guide 429 disposed in the elongated body 402. The guide 429 defines a hole 432 with an inside diameter 433 that is larger than an outside diameter 431 of the guiding end 430 of the clamping device 426. The clamping end 428 of the clamping device has a first jaw member 434 and a second jaw member 436 opposing the first jaw member 434. First arm 435 and second arm 437 connect the guiding end to the first jaw member and second jaw member.

Typically, the first jaw member and the second jaw member are biased away from each other when they are in the relaxed position. Various methods can be used to bias the first and second jaw member away from each other. For example, the material used to make the clamping device may be a spring steel that will allow the first and second jaws to flex inward and outward. Alternatively, a spring 438 may be disposed between the first arm 435 and the second arm 437.

As shown in FIG. 12B, the internal dimension 474 of the first end 414 of the elongated body 402 is approximately the same as an external dimension 472 of the first and second jaw members when the members are in a closed position. As such, when the actuator 418 moves to a most rearward position being pushed in the direction of arrow 422 it drives the first jaw member and the second jaw member towards each other, causing the jaw members to clamp together. When the actuator 418 is moved forward in the direction of arrow 420, the first and second jaw members spring away from each other and the jaws open.

A serrated edge 440 having teeth 442 is disposed on an interior portion 441 of the first end 404 of the elongated by body 402. Affixed to the actuator 418 is a locking device 444 with a tooth 446 on a distal end 452 of the flexible bar 448 that mates with the teeth 442. As shown in FIG. 4, a proximal end 454 of the flexible bar 448 is affixed to the actuator 418. Alternatively, there may be a single tooth disposed on the interior portion 441 of the first elongated body and multiple teeth disposed on the distal end 452 of the flexible bar 448. As with the embodiment shown in FIG. 2A, the jaws of the embodiment of FIG. 12A may have reliefs or knurled gripping surfaces or both, and one jaw may have a pin that aligns with a hole in the other jaw to prevent lateral movement.

Figure 13:
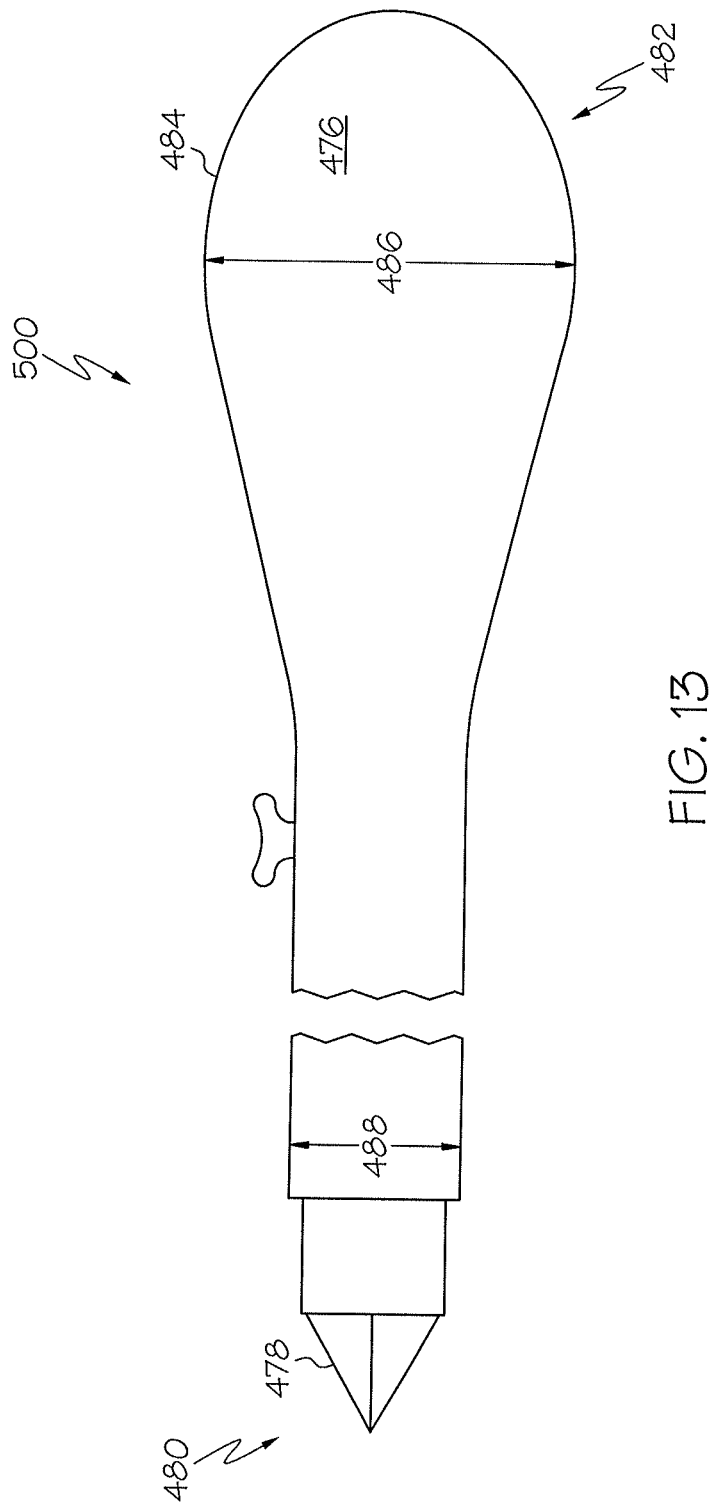
FIG. 13 is a side view of another embodiment of a needle driver having a bulbous second end.

FIG. 13 shows a needle driver 500 with jaws 478 on a first end and a bulbous end 476 disposed on a second end 482 of the needle driver. The bulbous end 476 has a rounded portion 484 that has an outside diameter 486 that is larger than an outside diameter 488 of the first end 480. The bulbous end is sized to fit the hand of a user to allow the user to palm the needle driver instead of holding it between the user's fingers. The bulbous end could also be included as a feature on other embodiments of a needle driver described herein.

Figure 14:
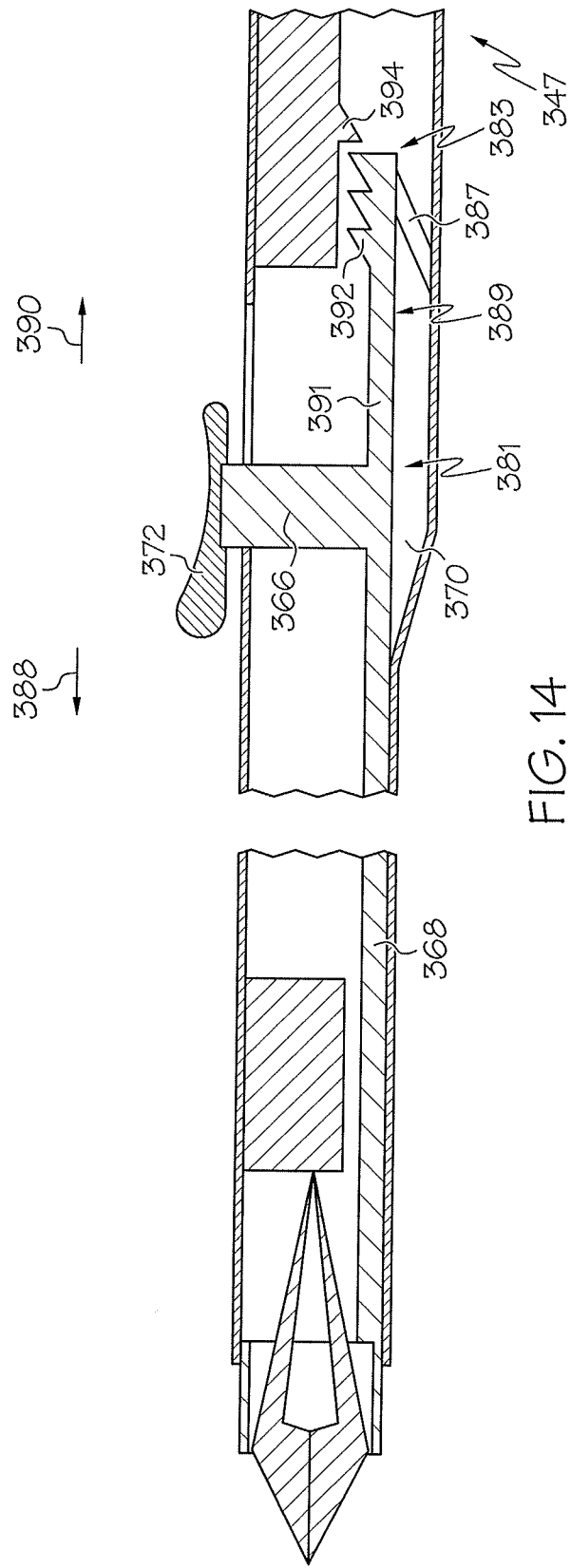
FIG. 14 is a section view of another embodiment of a needle driver of the invention.

FIG. 14 shows an embodiment similar to that of FIG. 10, with the rotatable actuator 320 of FIG. 10 replaced with a slideable actuator 366 affixed to a second end 370 of a shaft 368. A first end 381 of a flexible bar 391 is connected to the slideable actuator 366, and a second end 383 has teeth 392. A user pushes the actuator 366, which has a digit receiver 372, in the direction of arrow 388 to close the jaws. To open the jaws, the user pushes the digit receiver down to release a tooth 394 from the teeth 392 and slides the digit receiver in the direction 390. A spring 387 biases against an underside 389 of a flexible bar 391 to maintain engagement of the teeth 392 with the tooth 394. When the operator pushes the slideable actuator 366 down, it compresses spring 387 and unlocks teeth 392 from tooth 394. While not shown in FIG. 14, a handle, such as handle 348 of FIG. 9A, is typically included on a second end 347. Alternatively, a handle with a bulbous end such as that shown in FIG. 13 may be disposed on the second end 347.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention is therefore not limited to the specific details, representative apparatus and method, and illustrated examples shown and described. Accordingly, departures may be made from such details without departing from the scope or spirit of the invention.

What is claimed is:

1. A needle driver, comprising:
 a first elongated body comprising a substantially hollow interior portion, a first, distal end and a second, proximal end;
 a second elongated body comprising a substantially hollow interior portion, a first, distal end and a second, proximal end, the second elongated body being slideably disposed in the first elongated body, and slideable between a rearward, retracted position and a forward, extended position;
 a clamping device comprising a clamping end and a connected end, the clamping device being at least partially disposed in the first elongated body and in the second elongated body, wherein the connected end is affixed to the first elongated body;
 a slideable actuator affixed to the second elongated body; and
 a locking device mating with the second elongated body; wherein
 the first, distal end of the second elongated body extends beyond the first, distal end of the first elongated body when the second elongated body is in the forward, extended position;
 the first, distal end of the second elongated body is disposed within the first, distal end of the first elongated body when the second elongated body is in the rearward, retracted position;
 the first elongated body and the second elongated body cooperate to define an annular space;
 the first elongated body further comprises at least one tooth;
 the first, distal end of the first elongated body comprises an interior portion;

the at least one tooth is disposed on, and extends inwardly from, the interior portion of the first, distal end of the first elongated body into the annular space;

the locking device is configured for engagement with the at least one tooth of the first elongated body, the locking device being operable for selectively locking the actuator in a predetermined number of positions;

the clamping end of the clamping device comprises a first jaw member and a second jaw member; and the first jaw member and the second jaw member are spaced from each other when the second elongated body is in the rearward, retracted position and move toward each other as the second elongated body slides toward the forward, extended position.

2. The needle driver according to claim 1, wherein:

the first jaw member comprises a pin and the second jaw member defines a hole sized to receive the pin to align the first and second jaw members; and the first jaw member and the second jaw member are biased away from each other.

3. The needle driver according to claim 1, wherein:

the at least one tooth of the first elongated body comprises a serrated edge disposed on the interior portion of the first, distal end of the first elongated body, the serrated edge comprising a plurality of teeth extending inwardly from the interior portion of the first, distal end of the first elongated body into the annular space.

4. The needle driver according to claim 3, wherein:

the locking device comprises a flexible bar, the flexible bar comprising a distal end and a tooth disposed on the distal end and configured for engagement with the teeth of the serrated edge of the first elongated body.

5. A needle driver, comprising:

a first elongated body comprising a substantially hollow interior portion, a first, distal end and a second, proximal end;

a second elongated body comprising a substantially hollow interior portion, a first, distal end and a second, proximal end, the second elongated body being slideably disposed in the first elongated body, and slideable between a rearward, retracted position and a forward, extended position;

a clamping device comprising m in end and a connected end, the clamping device being at least partially disposed in the first elongated body and in the second elongated body, wherein the connected end is affixed to the first elongated body;

a slideable actuator affixed to the second elongated body; and a locking device mating with the second elongated body; wherein the first, distal end of the second elongated body extends beyond the first, distal end of the first elongated body when the second elongated body is in the forward, extended position;

the first, distal end of the second elongated body is disposed within the first, distal end of the first elongated body when the second elongated body is in the rearward, retracted position;

the clamping end of the clamping device comprises a first jaw member and a second jaw member;

the first jaw member and the second jaw member are spaced from each other when the second elongated body is in the rearward, retracted position and move toward each other as the second elongated body slides toward the forward, extended position;

the needle driver is devoid of a biasing member engaged with the second elongated body, the second elongated body being unbiased toward the forward, extended position;

the clamping device further comprises a first arm and a second arm;

the first arm connects the first jaw member to the connected end of the clamping device;

the second arm connects the second jaw member to the connected end of the clamping device;

each of the first arm and the second arm tapers inwardly from the clamping end toward the connected end;

the second elongated body contacts the first arm and the second arm adjacent the first jaw member and the second jaw member, respectively, when the second elongated body is in the forward, extended position;

the first elongated body and the second elongated body cooperate to define an annular space;

the first, distal end of the first elongated body comprises an interior portion;

the first elongated body further comprises a serrated edge disposed on the interior portion of the first, distal end of the first elongated body, the serrated edge comprising a plurality of teeth extending inwardly from the interior portion of the first, distal end of the first elongated body into the annular space; and the locking device comprises a flexible bar, the flexible bar comprising a distal end and a tooth disposed on the distal end and configured for engagement with the teeth of the serrated edge of the first elongated body.

6. A needle driver, comprising:

a. a first elongated body comprising a substantially hollow interior portion, at least one tooth, a first, distal end and a second, proximal end, the first, distal end comprising an interior portion;

b. a second elongated body comprising a substantially hollow interior portion, the second elongated body being slideably disposed in the first elongated body, and slideable between a rearward, retracted position and a forward, extended position;

c. a clamping device comprising a clamping end and a connected end, the clamping device being at least partially disposed in the first elongated body and in the second elongated body, wherein the connected end is affixed to the first elongated body;

d. a slideable actuator affixed to the second elongated body; and e. a locking device mating with the second elongated body and configured for engagement with the at least one tooth of the first elongated body, the locking device being operable for selectively locking the actuator in a predetermined number of positions; wherein f. the clamping end of the clamping device comprises a first jaw member and a second jaw member;

g. the first jaw member and the second jaw member are spaced from one another when the second elongated body is in the rearward, retracted position and move toward each other as the second elongated body slides toward the forward, extended position;

h. the first elongated body and the second elongated body cooperate to define an annular space; and i. the at least one tooth is disposed on, and extends inwardly from, the interior portion of the first, distal end of the first elongated body into the annular space.

7. The needle driver of claim 6, wherein:

the at least one tooth of the first elongated body comprises a serrated edge disposed on the interior portion of the first, distal end of the first elongated body, the serrated edge comprising a plurality of teeth extending inwardly from the interior portion of the first, distal end of the first elongated body into the annular space; and the locking device comprises a flexible bar, the flexible bar comprising a distal end and a tooth disposed on the distal end and configured for engagement with the teeth of the serrated edge of the first elongated body.

\* \* \* \* \*